United States Patent [19]

Holzhauer et al.

[11] Patent Number: 5,097,066

[45] Date of Patent: Mar. 17, 1992

[54] PROCESS FOR PURIFICATION OF AROMATIC DICARBOXYLIC ACIDS

[75] Inventors: Juergen K. Holzhauer; George E. Kuhlmann, both of Naperville, Ill.

[73] Assignee: Amoco Corporation, Chicago, Ill.

[21] Appl. No.: 545,291

[22] Filed: Jun. 27, 1990

[51] Int. Cl.⁵ .............................................. C07C 51/47
[52] U.S. Cl. ................................... 562/487; 562/485; 562/486
[58] Field of Search .................... 562/487, 485, 486

[56] References Cited

U.S. PATENT DOCUMENTS

| | | | |
|---|---|---|---|
| 3,574,727 | 4/1971 | Taylor et al. | 562/487 |
| 3,592,847 | 7/1971 | Gailivan et al. | 562/487 |
| 4,370,496 | 1/1983 | Shigeyasu et al. | 562/487 |

Primary Examiner—Jose G. Dees
Assistant Examiner—Vera C. Clarke
Attorney, Agent, or Firm—Thomas E. Nemo; William H. Magidson; Ralph C. Medhurst

[57] ABSTRACT

Aromatic dicarboxylic acids, specifically 4,4'-dicarboxydiphenyl ether, terephthalic acid, 4,4'-carboxybis(benzoic acid) and the like, are purified by dissolving the crude acid in a monocarboxylic acid anhydride, purifying the resulting solution, and recovering a purified acid product therefrom.

19 Claims, 2 Drawing Sheets

PROCESS FOR PURIFICATION OF AROMATIC DICARBOXYLIC ACIDS

TECHNICAL FIELD OF THE INVENTION

This invention relates to a process for purifying aromatic dicarboxylic acids. Specifically, purification is effected by dissolving the acid in a monocarboxylic acid anhydride, purifying the resulting solution by adsorption, absorption, oxidation, reduction, recrystallization or combinations thereof, and recovering the purified acid by hydrolysis, or recrystallization or a combination of the two techniques.

BACKGROUND OF THE INVENTION

Aromatic dicarboxylic acids are commercially important as raw materials in the manufacture of high molecular weight polymers, such as polyethylene terephthalate, which is used in making synthetic fibers, films and the like products. Methods for manufacturing aromatic carboxylic acids are numerous. Methods for producing aromatic dicarboxylic acids are disclosed in U.S. Pat. No. 4,855,492 to Hundley et al. and U.S. Pat. Nos. 4,709,080 and 4,772,742 to Spanswick et al. Another method specifically for synthesizing terephthalic acid is disclosed in U.S. Pat. No. 4,185,073 to Marsh et al.

In order to be useful as a raw material for polymer manufacture, the aromatic dicarboxylic acid monomer must have relatively high purity prior to polymerization. Unfortunately, conventional processes often produce such carboxylic acid monomers with excessive amounts of colored and color-forming impurities as well as metal compounds that must be reduced.

Most aromatic dicarboxylic acids are produced by the oxidation of alkyl aromatic compounds. Impurities, such as, for example, aromatic aldehyde and ketone impurities, result from incomplete oxidation of those compounds and must also be removed from the resultant aromatic dicarboxylic acids. Unfortunately, because of the varying characteristics of the impurities present, solvents that will remove the aromatic aldehyde and ketone impurities do not necessarily effectively remove the color-forming or metal impurities that are present as well. Also, purification processes that effectively purify other materials are ineffective for purifying aromatic dicarboxylic acids because of the insolubility of these aromatic acids in conventional solvents.

Crystallization techniques, such as the one disclosed in British Patent No. 1,271,779 to Witt, have been employed to remove aromatic aldehydes and ketones as well as color-forming and metal impurities from aromatic dicarboxylic acids. The crystallization technique disclosed in Witt, however, requires rather severe processing conditions, i.e., temperatures of 300° to 325° C. Furthermore, the aromatic dicarboxylic acid is purified in a solution of phenol and water. Phenol is a toxic substance, and employee exposure to this material should be minimized. Finally, the phenol esterifies the carboxylic acid, resulting in the loss of a portion of the desired product. These factors make the Witt recrystallization process undesirable.

Another process utilized to purify carboxylic acids requires the conversion of the acids to dimethyl esters, which are reasonably soluble in hydrocarbons and which have sufficiently high vapor pressures to permit distillation of the resulting mixtures. This conversion/purification technique is costly and time consuming as well.

Prior art processes specific for the purification of terephthalic acid are described in U.S. Pat. No. 3,574,727 to Taylor et al. and U.S. Pat. No. 3,592,847 to Gallivan et al. The Taylor et al. process consists of dissolving the terephthalic acid in a mixture of lower alkanoic acid and lower alkanoic anhydride and recrystallizing the purified terephthalic acid from the solution. The Gallivan et al. process purifies terephthalic acid by dissolving 5 to 20 weight percent of the acid in a heated solution of acetic anhydride to produce a supersaturated solution. Any excess crude terephthalic acid which may have been added to the anhydride and remains undissolved in the solution is filtered from the solution, preferably before the addition of a lower alkanoic acid (e.g. acetic acid), to oxidize the resultant terephthalic acid is then recovered by recrystallization.

SUMMARY OF THE INVENTION

The present invention provides a relatively inexpensive process for effective purification of crude aromatic dicarboxylic acids. This is accomplished by dissolving these acids in an excess by weight of a monocarboxylic acid anhydride, purifying the resulting solution by adsorption, absorption, oxidation, reduction, recrystallization, or combinations thereof, and thereafter recovering a purified solid product, usually by hydrolysis or recrystallization.

Preferably, one part by weight of the aromatic dicarboxylic acid to be purified is dissolved in at least about three parts by weight of the monocarboxylic acid anhydride to form mixed mono- or polyanhydrides, and the resulting solution is then purified by, for example, adsorption, absorption, oxidation, reduction, recrystallization or combinations thereof. The mixed acid anhydrides are then recovered from the resulting admixture and then hydrolyzed to aromatic dicarboxylic acids of relatively high purity. The hydrolyzed material can be recrystallized further to provide a product of even greater purity.

DETAILED DESCRIPTION OF THE PREFERRED EMBODIMENT

The present process for purification of aromatic dicarboxylic acids, such as 4,4'-dicarboxydiphenyl ether (DCDPE), terephthalic acid (TA), 4,4'-carboxybis(benzoic acid) (4,4'-CBBA), and the like, uses a monocarboxylic acid anhydride containing 4 to 18 carbon atoms, inclusive, as solvent. An alkanoic acid anhydride containing from 4 to 8 carbon atoms, a benzoic acid anhydride or toluic acid anhydride can be employed as a reactive purification solvent for this purpose. The monocarboxylic acid anhydride can be represented by the general formula

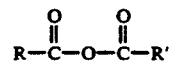

wherein R and R' are alkyl or aryl groups that can be the same or different, and in which the total number of carbon atoms does not exceed sixteen.

The advantages of purifying the above-stated dicarboxylic acids using the instant process are numerous. Firstly, the process does not discolor the crude product, which, as stated above, is very important if the purified product is to be used in the manufacture of polymers. Moreover, aromatic acids such as 4,4'-CBBA, not readily soluble in common organic solvents, can be easily purified by this process. The present process also provides relatively good recovery of the starting material. Very little of the aromatic dicarboxylic acid is lost in the purification process.

In addition, the present purification process is compatible with the existing equipment used for oxidizing aromatic dicarboxylic acids, since the oxidation process utilizes the acids of the acid anhydrides used herein as the purification solvent. Yet another advantage of the present purification process is that it introduces no new impurities into the process.

To effect the desired purification, preferably the monocarboxylic acid anhydride is combined with the crude aromatic dicarboxylic acid to be purified in a weight ratio of at least about 3:1.

Figure 1:
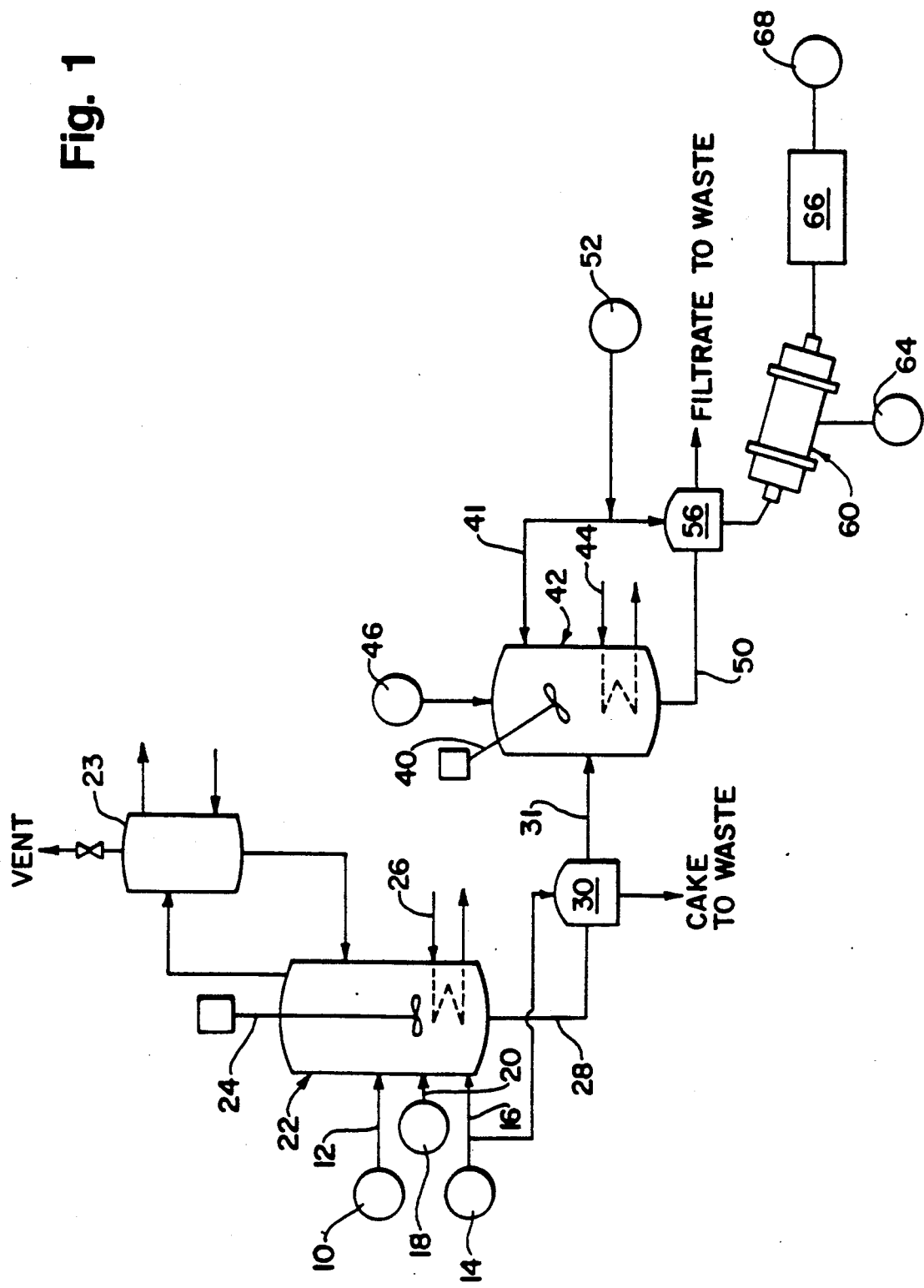
FIG. 1 is a flow diagram of a process embodiment where the purified material is recovered by hydrolysis.

Referring to FIG. 1, the aromatic dicarboxylic acid to be purified from source 10 and the purification solvent from source 14 are charged into vessel 22, equipped with reflux condenser 23, via lines 12 and 16 respectively. The resulting mixture of mono- and poly-anhydrides is stirred using mixer 24, heated to reflux by heating means such as coils 26 and maintained at reflux for a time period sufficient to form mixed anhydrides. After the dicarboxylic acid and the purification solvent, such as acetic anhydride, are dissolved completely, decolorizing carbon is added to the vessel 22 via line 20 from source 18. The resulting mixture is stirred for an extended time period, usually approximately 1 hour. Then the contents of vessel 22 is drained via line 28 into the filter 30. The filtrate from filter 30, containing the dissolved aromatic dicarboxylic acid is conveyed via line 31 to hydrolysis vessel 42. The filtercake is washed with an aliquot of the purification solvent and then discarded.

The admixture of filtrate from the filter 30 and purification solvent 14 is heated by heater 44 in vessel 42 while the admixture is stirred by mixer 40. Water from source 52 is added gradually to the admixture via line 41 while the admixture is stirred to produce a slurry. The resulting slurry is drained from the vessel 42 via line 50 and filtered in filter 56. The filtrate is discarded, or in an alternate embodiment, it can be purified and recycled. The solid product is washed with water from source 52. The washed product is recovered and then dried in drier 60 under vacuum (usually about 20" of Hg) generated by a vacuum source such as pump 64. The dried product is then hydrolyzed in a suitable vessel 66 using standard hydrolysis techniques. The resulting product is conveyed to appropriate storage 68 and has less impurities than the starting material 10.

Figure 2:
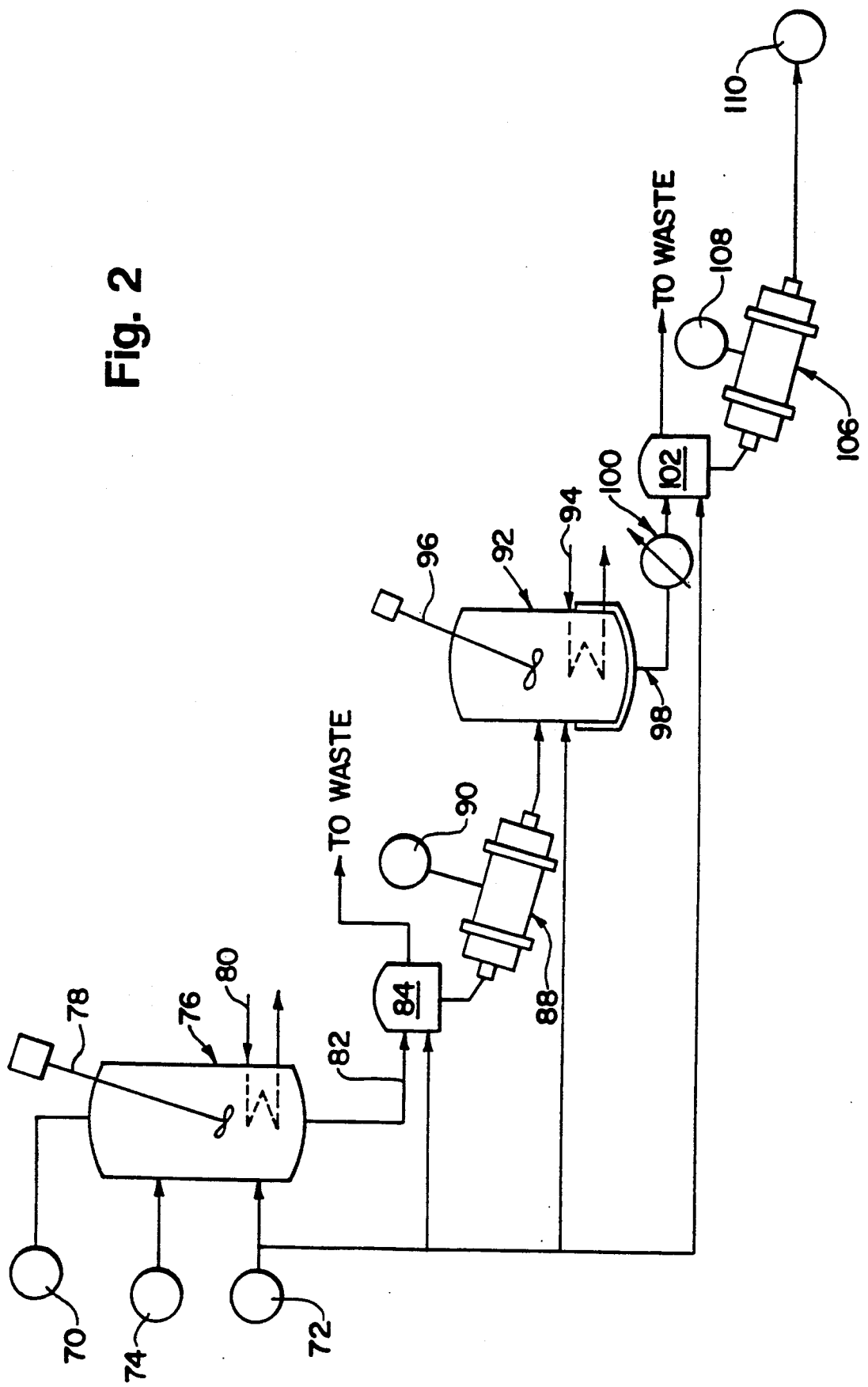
FIG. 2 is a flow diagram of a process embodiment where the purified material is recovered by hydrolysis followed by recrystallization.

Referring to FIG. 2, a solution of an aromatic dicarboxylic acid in an acid anhydride from source 70 is combined with hydrolysis acid from source 72 and water from source 74 in vessel 76. The hydrolysis acid, for example, acetic acid, is added over a period of time, approximately one hour, optionally followed by the addition of water. The resulting admixture is stirred by mixer 78 and optionally heated by a heating source such as heater coil 80. A slurry results. The slurry is conveyed via line 82 to filter 84 for filtering. The obtained filtrate is discarded to waste. The filtercake is washed with an aliquot of hydrolysis acid from source 72 and then dried in drier 88. The drier is operated at a reduced pressure generated by vacuum source 90, usually at about 20 inches of Hg. The resulting dried material is placed in an autoclave 92 equipped with a heating element 94 and stirrer 96. Hydrolysis acid from source 72 is added to the autoclave 92 and the obtained admixture is heated. The resulting slurry is drained from the autoclave 92 via line 98 and then cooled in heat exchanger 100. The cooled slurry is then filtered by filter 102. The resulting filtrate is discarded and the solid product from filter 102 is washed using hydrolysis acid 72. The solid product from filter 102 is then dried in drier 106 under vacuum drawn by vacuum source 108. The dried product 110 is markedly improved in purity over the crude aromatic dicarboxylic acid feed.

The following examples are for purposes of illustration only, and highlight the concepts embodied by this invention. The optical density (O.D.) of the starting materials and the products as reported in Examples I–VI below was determined by dissolving the purified aromatic dicarboxylic acid (0.5 gram in a 3N solution of KOH (30 ml)) and then measuring the absorbance of 340 nm wavelength by the resulting solution in a 10 mm cell. The measured absorbance ($A_{340}$) was then normalized to the standard 50 mm path length, i.e., O.D.=5-×($A_{340}$).

EXAMPLE I

Purification of 4,4'-Dicarboxydiphenyl Ether Using Activated Carbon

In a 300 ml flask equipped with stirrer, heating mantle and reflux condenser, acetic anhydride (100 grams) and crude 4,4'-dicarboxydiphenyl ether (DCDPE; 10 grams) were heated to reflux. The DCDPE was dissolved completely. Decolorizing carbon (Nuchar S-N; 0.2 grams) was added to the solution. The resulting admixture was stirred for about one hour and then filtered through a bed of diatomite filter aid. The filter was subsequently washed with a 10-gram aliquot of hot acetic acid anhydride. The wash liquid was combined with the filtrate. The temperature of the filtrate was adjusted to 100° C. (212° F.). Water was gradually added to the filtrate while stirring. The resulting slurry was filtered hot, and the obtained filtercake was washed with hot water (20 grams), then dried for 16 hours at a reduced pressure (20" of Hg vacuum). The overall solids recovery was 80.1 percent. The color of the recovered solids was much improved over that of the starting material. The optical density of the recovered solids was observed to be 0.48, compared to 1.14 for the starting material.

A part of the obtained filtercake was hydrolyzed with potassium hydroxide. The resulting solution was acidified, and the amount of acetic acid present was measured by gas chromatography. Assuming that all the acetic acid came from the mono-anhydride of acetic acid and DCDPE, the content of mono-anhydride in the product was observed to be 3.6 mole percent.

EXAMPLE II

Purification of 4,4'-Dicarboxydiphenyl Ether Without Activated Carbon

An aliquot of DCDPE was dissolved in acetic acid anhydride, and the product was subsequently crystallized by cooling. The product was filtered and dried. It was then refluxed with water for an hour, filtered, washed and dried. The dried cake contained about 5 mole percent of the corresponding monoanhydride. The optical density was observed to be 1.3, as compared to 1.14 for the starting material. Therefore, the absence of activated carbon did not allow for a low optical density of the recrystallized product as it did in EXAMPLE I.

EXAMPLE III

Purification of Extremely Impure 4,4'-Dicarboxydiphenyl Ether Using Activated Carbon An aliquot of DCDPE having an optical density greater than 15 was purified in a manner similar to that described in Example I. The amount of acetic acid anhydride used was 3 grams per gram of DCDPE. Even at this relatively low concentration, the DCDPE dissolved completely at reflux. Since the starting material was much darker than the starting material used in Example I, the activated carbon concentration added to the refluxing solution was increased to 0.05 grams per gram of DCDPE. The recovery of hydrolyzed product was 92 percent, and the mono-anhydride content thereof was 4.7 mole percent. Although the product was off-white, with an observed optical density of 8.08 its color was much improved over that of the starting material.

EXAMPLE IV

Purification of Extremely Impure 4,4'-Dicarboxydiphenyl Ether Using Acetic Acid in the Hydrolysis Solution The experiment of Example III was repeated except that acetic acid was added to the hydrolysis solution to prevent excessive thickening of the resulting slurry. The optical density of the product was observed to be 7.08, a marked improvement over that of the starting material.

EXAMPLE V

Purification of 4,4'-Dicarboxydiphenyl Ether Using An additional Recrystallization Step Crude DCDPE (100 grams) and acetic acid anhydride (300 grams) were combined and heated to reflux. After the resulting solution had cleared, activated carbon (Nuchar S-N; 2 grams) a decolorization material, was added to the solution and the resulting mixture stirred for 30 minutes. The mixture was then filtered through a diatomite filter aid. The filter was then washed with 50 grams of hot acetic acid anhydride and the wash liquid combined with the filtrate. With the temperature of the obtained mixture maintained at 93° C. (200° F.), an aqueous acetic acid solution (95% conc.; 228 grams) was added thereto over a period of one hour. Subsequently, water (72 grams) was added thereto over a period of 30 minutes. The resulting slurry was filtered hot and washed with a hot aqueous solution of acetic acid (95% conc.; 50 grams). The obtained cake was then dried for 16 hours at 90° C. (194° F.) and at a reduced pressure (20" of Hg vacuum). The optical density of the obtained dried product was observed to be 0.625 which compared favorably to an observed optical density of 1.48 for the starting material. The dried product contained 121 parts of ash per million parts by weight, which compares very favorably with the 1540 parts of ash per million parts by weight in the starting material. The solids recovers from the process was 95.8 percent by weight.

The recovered purified material (75 grams) and an aqueous solution of 95 percent acetic acid (300 grams) were charged to a one-liter titanium autoclave equipped with a heater and a magnetic stirrer. The material was dissolved by heating the mixture to about 240° C. (about 464° F.). The solution with the dissolved product therein was then cooled to about 71° C. (about 160° F.), filtered, and washed with an aqueous solution of hot 95 percent acetic acid (75 grams). The obtained cake was subsequently dried for 16 hours at 90° C. (194° F.) and at a reduced pressure (20" of Hg vacuum). The optical density of the dried product was measured at 0.325. The solids recovery was 91.6 percent for the recrystallization portion of the process, and 87.8 percent for the overall process.

EXAMPLE VI

Purification of Terephthalic Acid

Terephthalic acid (TA; 10 grams) was dissolved in acetic acid anhydride (267 grams) by heating a TA and acetic acid anhydride mixture to reflux. The resulting solution was then treated with activated carbon (Nuchar S-N; 0.4 grams) for 30 minutes and filtered through diatomaceous earth. The filter was subsequently washed with a 10-gram aliquot of hot acetic acid anhydride. The temperature of the resultant filtrate was adjusted to about 104° C. (about 220° F.) and water (63.6 grams) was added gradually to this solution over a time period of one hour. The resulting slurry was filtered, and the obtained filtercake was washed with hot water (10 grams). The filtercake was then dried for 16 hours at 90° C. (194° F.) and at a reduced pressure (20" of Hg vacuum). The optical density of the obtained purified product was found to be 0.414, which value compares favorably to the optical density of 0.765 for the starting material.

Tables I and II below summarize the data from Examples I-VI set forth above.

TABLE I

Purification of DCDPE

| | EXAMPLE | | | |
|---|---|---|---|---|
| | I | II | III | IV |
| Feed Optical Density | 1.14 | 1.14 | >15 | >15 |
| Acetic Anhydride, g/g DCDPE | 10 | * | 3 | 3 |
| Carbon, g/g DCDPE | 0.02 | — | 0.05 | 0.05 |
| Acetic Anhydride g/g DCDPE | 0.1 | — | — | — |
| Hydrolysis Solution: | | | | |
| Water, g/g DCDPE | 10 | 20 | 1 | 0.9 |
| Acetic Acid, g/g DCDPE | — | — | — | 3 |
| Water Wash, g/g DCDPE | 2 | 2 | 1 | 1 |
| Solids Recovery, wt. % | 80.1 | 92 | 90.8 | 88.2 |
| Monoanhydride, Mole Percent | 3.6 | 5 | 4.7 | 5.8 |
| Product Optical Density | 0.48 | 1.30 | 8.08 | 7.08 |

*Starting material was crystallized from acetic anhydride; a mixture of mono- and di-anhydrides with acetic acid.

TABLE II

Purification of Aromatic Acids

| | EXAMPLE | | |
|---|---|---|---|
| | V | V* | VI |
| Feed Type | DCDPE | DCDPE | TA |
| Feed Optical Density | 1.48 | 0.625 | 0.765 |
| Feed Ash, ppm | 1540 | 121 | N/A |
| Water, g/g Feed | — | 0.2 | — |
| Acetic Acid, g/g Feed | — | 3.8 | — |
| Acetic Anhydride, g/g Feed | 3 | — | 13.4 |
| Carbon; g/g Feed | 0.02 | — | 0.02 |
| Hydrolysis Solution: | | | |
| Water, g/g Feed | 0.834 | — | 3.18 |
| Acetic Acid, g/g Feed | 2.166 | — | — |
| Wash Solution: | | | |
| Water, g/g Feed | 0.025 | 0.05 | 0.5 |
| Acetic Acid, g/g Feed | 0.475 | 0.95 | — |
| Solids Recovery, % | 95.8 | 91.6 | 98.0 |
| Product Optical Density | 0.625 | 0.325 | 0.414 |
| Product Ash, ppm | 121 | 84 | N/A |

*The additional recrystallization step of Example V.
NA = Not Available

EXAMPLE VII

Purification of 4,4'-Carboxybis(benzoic) acid

Crude 4,4'-CBBA was prepared by the oxidation of 4,4'-carboxybistoluene according to the process disclosed in U.S. Pat. No. 4,772,742 to Spanswick et al. The crude 4,4'-CBBA (14.3 grams) was dissolved in acetic anhydride (204 grams) in a molar ratio of 40:1. The dissolution took place at an elevated temperature of 125° C. (257° F.). Peracetic acid (4 grams) as an oxidizing agent was added to the heated mixture after the mixture was cooled to 60° C. (140° F.). The mixture was further cooled to about 30° C. (86° F.). The 4,4'-CBBA mixed anhydride crystallized from the solution. The crystals were removed by filtration and the wet cake washed with acetic anhydride (25 ml).

The filtered crystals were redissolved in acetic anhydride (204 grams) in an amount effective to solubilize the mixed anhydride bonds in the crystals. The mixture was heated to 80° C. (176° F.) with a solution of acetic acid (60 grams) and water (40 grams) to hydrolyze the anhydride bonds and solubilize residual oxidation catalyst metals that remained in the crystals. The aqueous acetic acid solution was added in 10 ml increments to limit heat evolution. The solution temperature was maintained at 90° C. (194° F.) or less. These metals were removed from the purified product by hot filtration at 80° C. (176° F.). The wet cake was washed with acetic acid (100 ml at 80° C. (176° F.). The filtercake contained purified 4,4'-CBBA.

Several preparations were made according to the above procedure and the products were analyzed for purity and yield. The results are tabulated below.

The crude and purified products were tested for optical density to determine the effectiveness of the process for removing color impurities. A 0.1 gram sample of the 4,4'-CBBA was dissolved in 30 ml of a 3N aqueous solution of potassium hydroxide (KOH). The KOH solution was made by dissolving 168 grams of KOH in 1 liter of distilled water. The solution was placed in a 10 mm cell. The absorbance of the solution was determined within 10 minutes at 340 nm on a dual beam spectro-photometer with 3.0 N KOH solvent in the reference beam. The optical density was calculated for 4,4'-CBBA by multiplying the absorbance by 5.0 (i.e., $OD_{340}=5 \times A^{340}$) to normalize the absorbance to the standard 50 mm path length.

TABLE III

Crude 4,4'-CBBA Analysis

| | Preparation | | | | | | | | | Total |
|---|---|---|---|---|---|---|---|---|---|---|
| | 1 | 2 | 3 | 4 | 5 | 6 | 7 | 8 | 9 | (Avg.) |
| Acid Number (Theoretical = 392 mg/g) | 426 | 419 | 423 | 429 | 433 | ND[1] | ND[1] | ND[1] | ND[1] | (426) |
| Inorganic Impurities, ppm[2] | | | | | | | | | | |
| Co | 44 | 63 | 41 | 52 | 48 | " | " | " | " | (50) |
| Mn | 36 | 51 | 32 | 41 | 36 | " | " | " | " | (39) |
| Br | 265 | 460 | 276 | 301 | 362 | " | " | " | " | (333) |
| Optical Density | 12 | ND[1] | 11 | ND[1] | 15 | " | 13 | " | 13 | (13) |
| Organic Impurities[3] | | | | | | | | | | |
| TA (wt %) | 11.3 | " | 9.61 | " | 8.3 | " | 11.0 | " | 10.5 | (10.1) |
| Others (wt %) | 5.6 | " | 6.2 | " | 6.0 | " | 5.2 | " | 6.0 | (5.8) |

[1]Not Determined
[2]Measured by x-ray fluoroscopy (XRF)
[3]Measured by gas silation chromatography (SGC)

TABLE IV

Purified 4,4'-CBBA Analysis

| | | | | | | | Total (Avg.) |
|---|---|---|---|---|---|---|---|
| Purification Mixture | | | | | | | |
| Crude 4,4'-CBBA Preparation (See Table III) | 1 & 2 | 2 & 3 | 3 & 4 | 6 & 7 | 7 & 8 | 8 & 9 | |
| Crude 4,4'-CBBA weight, g | 172 | 172 | 172 | 172 | 172 | 172 | |
| Acetic Anhydride weight, g | 1448 | 1448 | 1448 | 1448 | 1448 | 1448 | |
| Purified Product Analysis | | | | | | | |
| Yield, g | 106 | 103 | 105 | 113 | 112 | 107 | 646 |
| Wt % based on crude 4,4'-CBBA | 61.8 | 60.2 | 60.9 | 65.7 | 65.2 | 62.6 | (62.7) |
| Acid No. (Theoretical = 392 mg/g) | 412 | 407 | 408 | 408 | 406 | 407 | (408) |
| Inorganic Impurities, ppm[2] | | | | | | | |
| Co | 14 | 20 | 20 | 17 | 12 | ND[3] | (14) |
| Mn | ND[3] | ND[3] | ND[3] | ND[3] | ND[3] | ND[3] | (ND) |

TABLE IV-continued

Purified 4,4'-CBBA Analysis

| | | | | | | | Total (Avg.) |
|---|---|---|---|---|---|---|---|
| Br | 98 | 113 | 89 | 126 | 94 | 74 | (99) |
| Optical Density | 2.72 | 4.52 | 4.21 | 4.87 | 5.42 | 4.08 | (4.30) |
| Organic Impurities[4] | | | | | | | |
| TA (wt. %) | 0.73 | 0.70 | 0.66 | 0.74 | 0.73 | 0.80 | (0.73) |
| Others (wt. %) | 0.29 | 0.31 | 0.27 | 0.31 | 0.49 | 0.38 | (0.34) |

[1]Preparation of the Crude 4,4'-CBBA were combined as indicated for purification.
[2]Measured by x-ray fluoroscopy (XRF)
[3]Not Detected
[4]Measured by silation gas chromatography (SGC)

TABLE V

Comparison of Crude and Purified 4,4'-CBBA

| Analysis | Average Crude | Average Pure | % Reduction |
|---|---|---|---|
| $OD_{340}$ Value | 13 | 4.3 | 66 |
| Inorganic Impurities, ppm | | | |
| Co | 50 | 14 | 72 |
| Mn | 39 | ND[1] | 100 |
| Br | 333 | 99 | 70 |
| Acid Number | 426 | 408 | 53[2] |
| (Theoretical = 392 mg/g) | | | |
| Organic Impurities, Wt % | | | |
| TA | 10.1 | 0.73 | 93 |
| Others | 5.8 | 0.34 | 94 |

[1]Not Detected
[2]Reduction in Acid Number in excess of the theoretical value of 392 mg/g The above examples are intended to illustrate the invention but are not intended to limit the invention in any manner. Modifications and variants thereof are within the spirit and scope of this invention and are included within the appended claims as those skilled in the art will readily appreciate.

We claim:

1. A process for the purification of a crude aromatic dicarboxylic acid selected from the group consisting of 4,4'-dicarboxydiphenyl ether and 4,4'-carboxybis (benzoic acid), comprising:
   a) dissolving the crude aromatic acid in an excess by weight of a liquid monocarboxylic acid anhydride containing from 4 to 18 carbon atoms to provide a solution of said aromatic dicarboxylic acid in said anhydride;
   b) removing impurities from the resulting anhydride solution so as to produce a purified solution; and
   c) recovering purified aromatic dicarboxylic acid in solid form from the purified solution by recrystallization or hydrolysis.

2. The process of claim 1 wherein the crude aromatic dicarboxylic acid is dissolved in an alkanoic, benzoic or toluic acid anhydride.

3. The process of claim 2 wherein the alkanoic acid anhydride is acetic acid anhydride.

4. The process of claim 3 wherein the anhydride solution is heated to the reflux temperature of the solution and maintained at the reflux temperature for a time period sufficient to form mixed anhydrides.

5. The process of claim 2 wherein the alkanoic, benzoic or toluic acid anhydride is combined with crude aromatic dicarboxylic acid in a weight ratio of at leas about 3:1.

6. The process of claim 1 wherein the crude aromatic dicarboxylic acid is dissolved in benzoic acid anhydride.

7. The process of claim 1 wherein the aromatic dicarboxylic acid is 4,4'-dicarboxydiphenyl ether.

8. The process of claim 7 wherein the 4,4'-dicarboxydiphenyl ether is dissolved in acetic anhydride.

9. The process of claim 8 further comprising heating the solution of dissolved aromatic dicarboxylic acid to the reflux temperature of the dissolved solution and maintaining the heated solution at reflux temperature for a time period sufficient to form mixed anhydrides.

10. The process of claim 1 wherein the aromatic dicarboxylic acid is 4,4'-carboxybis(benzoic acid).

11. The process of claim 10 wherein the 4,4'-carboxybis(benzoic acid) is dissolved in acetic anhydride.

12. The process of claim 11 further comprising heating the solution of dissolved crude aromatic dicarboxylic acid to the reflux temperature of the dissolved solution and maintaining the heated solution at reflux temperature for a time period sufficient to form mixed anhydrides.

13. The process of claim 1 wherein the impurities are removed in step b) by a technique selected from the group consisting of adsorption, absorption, oxidation, reduction, recrystallization and combinations thereof.

14. The process of claim 1 wherein the solid, purified product is recovered by filtration and dried.

15. The process of claim 1 wherein the solid, purified product is recovered by centrifugation and dried.

16. The process of claim 11 further comprising adding a purification solvent selected from the group consisting of a purification acid, water and mixtures thereof prior to recovering the purified aromatic dicarboxylic acid.

17. The process of claim 16 wherein the purification acid is acetic acid.

18. A process for the purification of a crude aromatic dicarboxylic acid selected from the group consisting of terephthalic acid, 4,4'-dicarboxydiphenyl ether and 4,4'-carboxybis (benzoic acid), comprising:
   a) dissolving the crude aromatic dicarboxylic acid in an excess by weight of a liquid monocarboxylic acid anhydride containing from 4 to 18 carbon atoms to provide a solution comprising a mixed acid anhydride of said aromatic acid;
   b) removing purities from the solution so as to produce a purified solution;
   c) separating said mixed acid anhydride from said purified solution; and
   d) hydrolyzing said mixed acid anhydride from step c) to produce purified aromatic dicarboxylic acid.

19. The process of claim 18 wherein said removing impurities comprises treating said solution with activated carbon followed by filtration to remove said activated carbon.

* * * * *

UNITED STATES PATENT AND TRADEMARK OFFICE
CERTIFICATE OF CORRECTION

PATENT NO. : 5,097,066
DATED : March 17, 1992
INVENTOR(S) : Holzhauer, et. al.

It is certified that error appears in the above-indentified patent and that said Letters Patent is hereby corrected as shown below:

Column 2, line, "the resultant terephthalic acid is then recovered by recrystallization." should read --the resultant terephthalicaldehydic acid back to terephthalic acid. The terephtalic acid is then recovered by recrystallization --.

Column 5, line 34, "8.08its color" should read --8.08, its color--

Column 6, line 7, "The solids recovers" should read --The solids recovery--.

Column 8, line 17, "(100 ml at 80°C. (176°F.)." should read -- (100 ml at 80°C (176°F)).--

Signed and Sealed this

Ninth Day of November, 1993

Attest:

BRUCE LEHMAN

Attesting Officer

Commissioner of Patents and Trademarks